United States Patent
Sawyer et al.

(10) Patent No.: US 9,895,343 B2
(45) Date of Patent: Feb. 20, 2018

(54) METHOD FOR TREATING TUMORS WITH CANNABINOIDS

(71) Applicant: GLIA LLC, Boston, MA (US)

(72) Inventors: Kenneth I. Sawyer, Cushing, ME (US); Wei-wei Chang, Boston, MA (US)

(73) Assignee: GLIA, LLC, Boston, MA (US)

( * ) Notice: Subject to any disclaimer, the term of this patent is extended or adjusted under 35 U.S.C. 154(b) by 0 days.

(21) Appl. No.: 15/170,418

(22) Filed: Jun. 1, 2016

(65) Prior Publication Data
US 2016/0271100 A1    Sep. 22, 2016

Related U.S. Application Data

(63) Continuation of application No. PCT/US2015/041156, filed on Jul. 20, 2015.

(60) Provisional application No. 62/026,887, filed on Jul. 21, 2014.

(51) Int. Cl.
| | |
|---|---|
| *A61K 31/352* | (2006.01) |
| *A61K 9/00* | (2006.01) |
| *A61K 31/05* | (2006.01) |
| *A61K 31/4745* | (2006.01) |
| *A61K 31/495* | (2006.01) |
| *A61K 39/395* | (2006.01) |
| *A61K 39/00* | (2006.01) |

(52) U.S. Cl.
CPC .......... *A61K 31/352* (2013.01); *A61K 9/0014* (2013.01); *A61K 31/05* (2013.01); *A61K 31/4745* (2013.01); *A61K 31/495* (2013.01); *A61K 39/3955* (2013.01); *A61K 2039/505* (2013.01)

(58) Field of Classification Search
CPC .... A61K 31/352; A61K 31/05; A61K 31/495; A61K 9/0014
USPC ................................. 514/18.4, 454
See application file for complete search history.

(56) References Cited

U.S. PATENT DOCUMENTS

| | | |
|---|---|---|
| 6,328,992 B1 | 12/2001 | Brooke et al. |
| 2010/0216734 A1 | 8/2010 | Barlow et al. |
| 2010/0273895 A1* | 10/2010 | Stinchcomb ......... A61K 9/0014 514/733 |
| 2011/0071157 A1 | 3/2011 | Danhof |
| 2011/0178114 A1 | 7/2011 | Aung-Din |

FOREIGN PATENT DOCUMENTS

| | | |
|---|---|---|
| WO | WO-2006/017892 A1 | 2/2006 |
| WO | WO-2014/018856 A1 | 1/2014 |

OTHER PUBLICATIONS

Head and Neck Cancers (reviewed Feb. 1, 2013), https://www.cancer.gov/types/head-and-neck/head-neck-fact-sheet, p. 1.*
Maor et al, Genes and Cancer (Jul. 2012), vol. 3(7-8), pp. 512-520.*
CannabisScience.com, Cannabis Science Extracts Kill Cancer Cells in Cancer Patients Being Treated Through its Licensed Distributor Rockbrook, 4-page article published online Feb. 22, 2011.*
CannabisScience.com, Cannabis Science Provides Physician's Documentation that Confirms Successful Treatment of Skin Cancer, 3-page article published online Apr. 6, 2011.*
CannabisScience.com; Cannabis Science Receives New Photos and Positive Feedback from Patient Three and an Oncologist about his Severe Squamous Cell Carcinoma, 4-page online article published Apr. 11, 2012.*
CannabisScience.com, Cannabis Science Releases New Photos on the Continual Improvement of Patient Three Who Suffers from Squamous Cell Carcinoma, 3-page online article published Jul. 30, 2012.*
Velasco et al, Mol Neurobiol (2007), vol. 36, pp. 60-67.*

* cited by examiner

*Primary Examiner* — Kathrien Cruz
*Assistant Examiner* — Janet L Coppins
(74) *Attorney, Agent, or Firm* — Cesari and McKenna, LLP

(57) ABSTRACT

A method for treating radiotherapy- or chemotherapy-induced cognitive or emotional impairment by topically administering a cannabinoid. Also provided is a method for treating a tumor by topically administering a cannabinoid together with radiotherapy and/or chemotherapy.

8 Claims, No Drawings

METHOD FOR TREATING TUMORS WITH CANNABINOIDS

CROSS-REFERENCE TO RELATED APPLICATIONS

The present application is a continuation of International Application No. PCT/US2015/041156, filed on Jul. 20, 2015, which claims the priority of Provisional Application No. 62/026,887, filed on Jul. 21, 2014. The content of both prior applications is hereby incorporated by reference in its entirety.

BACKGROUND

Field

This application relates to ameliorating radiotherapy- and chemotherapy-induced cognitive and emotional impairment and to treating cancer with cannabinoids.

Background Information

Chemotherapy-associated cognitive or emotional impairment, commonly known as chemo brain and chemo fog (chemo brain/fog) has become a scientifically recognized and established consequence of chemotherapy, particularly during treatment of head, neck, and breast cancer. For example, patients undergoing treatment for glioblastoma often demonstrate symptoms of chemo brain/fog following radiotherapy and chemotherapy.

This cognitive or emotional impairment can negatively affect memory, tasking, and decision making capabilities. Chemo brain/fog may be transient or long term, often impairing a patient's quality of life for years or decades after treatment is completed.

The development of chemo brain/fog is influenced by the intensity and severity of the chemotherapy treatment, the specific chemotherapy agent, concurrent radiation treatment, and the tumor type and site. Chemotherapy agents including taxanes, platinum compounds, vinca alkaloids, thalidomide, bortezomib, corticosteroids, and bevacizumab have all been implicated as causative agents of chemo brain/fog.

There is evidence that visuospatial working memory, defined as the ability to retain and manipulate information during brief tasks, is impaired in chemo brain/fog. It has been postulated that in chemotherapy-associated cognitive impairment, activation of the dorsolateral prefrontal cortex is impaired. The dorsolateral prefrontal cortex controls the intraparietal sulcus located within the posterior parietal cortex, which is the main storage site of visuospatial working memory. See Raffa, J. Clin. Pharm. Ther. 2013, 38:265-268. Although the mechanisms responsible for chemo brain/fog are not known, it is thought that excessive release of pro-inflammatory cytokines, especially TNF-α, induced by the chemotherapy agents plays an important role in neural impairment.

Cognitive behavioral therapy has been shown to be somewhat effective for treating chemo brain/fog. To date, no drugs have been approved for treating this condition.

As mentioned above, chemo brain/fog is more prevalent when treating specific types of tumors. For example, patients undergoing treatment for glioblastoma often demonstrate symptoms of chemo brain/fog following radiotherapy and chemotherapy. Long term follow-up of these patients with respect to chemo brain/fog is not possible, as more than 80% of glioblastoma patients die within two years of diagnosis.

Typically, glioblastoma is treated by surgical excision of the greatest amount of tumor possible, followed by focal radiotherapy and adjuvant chemotherapy. Complete removal of the tumor is often not possible due to the tumor's infiltrating nature.

Although a number of chemotherapy agents have been used for treatment of glioblastoma, none have been able to reverse tumor size or volume, or increase survival rate significantly. Chemotherapeutic agents with approved indications for glioblastoma include temozolomide, bevacizumab, lomustine, and carmustine, to be given either orally or as injections. Other chemotherapy agents that have been used for treating glioblastoma without specific regulatory approval include topotecan, irinotecan, procarbazine, vincristine, and carboplatin. None of these agents actually decrease the size of tumors, but may temporarily halt progression. Notably, glioblastoma is highly aggressive, with a high rate of recurrence after treatment is completed.

Cannabinoids have long been administered orally for ameliorating nausea resulting from chemotherapy. Numerous in vitro studies have shown that cannabinoids can have an antiproliferative effect on glioma cells. Cannabinoids have also been shown to prevent the expansion of tumors in vivo animal tumor models. Yet, none of the animal studies showed the reversal or reduction in size of a tumor as a result of cannabinoid treatment. See a review by Rocha et al., J. Neurooncol. 2014, 116:11-24. One human study in which tetrahydrocannabinol (THC), i.e., a cannabinoid, was instilled into a glioblastoma tumor failed to demonstrate a clear-cut benefit from the THC. See Guzman et al., British J. of Cancer 2006, 95:197-203.

A single study combining cannabinoids and temozolomide showed growth suppression of two different glioma tumor xenografts in nude mice as compared to temozolomide or cannabinoids alone. See Torres et al., Mol. Cancer Ther. 2011, 10:90-103. Notably, the cannabinoids in this study were directly injected into the tumors.

The need exists to develop effective therapies for intractable cancers such as glioblastoma and for ameliorating the side-effects of radiotherapy and chemotherapy with respect to brain function.

SUMMARY

To meet this need, a method for treating radiotherapy- or chemotherapy-associated cognitive or emotional impairment is provided. The method includes topically administering to a subject an effective amount of a composition containing a cannabinoid.

Also provided is the use of a topical cannabinoid composition for treating radiotherapy or chemotherapy-associated cognitive or emotional impairment in a subject.

Also provided is a method for treating a tumor. The method includes the steps of identifying a subject having a tumor or having had surgery to remove a tumor, and administering to the subject a chemotherapy agent, radiation, or both, and topically administering a composition containing a cannabinoid.

The details of one or more embodiments are set forth in the description and the examples below. Other features, objects, and advantages will be apparent from the detailed description of several embodiments and also from the claims.

DETAILED DESCRIPTION

As mentioned above, a method for treating radiotherapy or chemotherapy-associated cognitive or emotional impairment includes a step of topically administering an effective amount of a composition that contains a cannabinoid.

The cannabinoid can be, but is not limited to dronabinol, cannabinol, cannabidiol, $\Delta^9$-tetrahydrocannabinol, $\Delta^8$-tetrahydrocannabinol, 11-hydroxy-tetrahydrocannabinol, 11-hydroxy-$\Delta^9$-tetrahydrocannabinol, levonantradol, $\Delta^{11}$-tetrahydrocannabinol, tetrahydrocannabivarin, anandamide, virodhamine, noladin ester, 2-arachidonoylglycerol, and nabilone.

In a preferred embodiment, the cannabinoid is $\Delta^9$-tetrahydrocannabinol. In a particularly preferred embodiment, the cannabinoid is dronabinol.

Dronabinol, as used herein, refers to a pure isomer of $\Delta^9$-tetrahydrocannabinol, namely, (−)-trans-$\Delta^9$-tetrahydrocannabinol, also known as (6aR,10aR)-6a,7,8,10a-tetrahydro-6,6,9-trimethyl-3-pentyl-6H-dibenzo[b,d]-pyran-1-ol.

The method described above requires topical administration of a cannabinoid-containing composition. Topical administration can be, e.g., applying the composition to the skin or mucous membranes. In a preferred embodiment, the cannabinoid-containing composition is applied topically to the face to the regions that are outside of the palpebral part of the eye, or the back of the neck.

The palpebral part of the eye refers to the region of and around the eye associated with the palpebral component of the orbicularis oculi muscle group. The palpebral component of the muscles originates in the palpebral ligament and runs above and below the eye to the lateral angle of the eye, forming concentric circles around the eye. The palpebral part of the eye thus refers to the facial surface around the eye that corresponds to the location of the palpebral component of the orbicularis oculi muscle lying underneath the facial skin. Non-limiting examples of these regions include the forehead above the eyebrows, the temple area between the end of the eyebrow and the hairline including the temple region, the upper cheek, or the sides or bridge of the nose.

In a preferred embodiment, the cannabinoid-containing composition is applied to the forehead. In yet another embodiment, the composition is applied to one or both temple regions. In a further embodiment, the composition is applied to the upper cheek. Additionally, the composition can be applied to one or both sides or the bridge of the nose. In a particular embodiment, the composition is applied to two or more regions of the face simultaneously or sequentially, and proximately or distant in time. For example, the composition can be applied to the forehead, and further applied to the temple region at the same time or at the next prescribed time, whether such next prescribed time is the same day or a different day. In one embodiment, the composition is applied to the same region of the face each time it is applied. In another embodiment, the composition is applied to any area of the skull, exclusive of the palpebral part of the eye. In a further embodiment, the composition can be applied intranasally to the mucous membrane inside of the nose. In a particular embodiment, the composition is applied to the back of the neck.

As mentioned above, the method for treating radiotherapy or chemotherapy-associated cognitive or emotional impairment requires topically administering an effective amount of a composition that contains a cannabinoid.

The effective amount of cannabinoid that is administered by this method can range from 0.01-30 mg per day. For example, the dose of cannabinoid topically applied can be 0.01 mg, 0.05 mg, 0.1 mg, 0.2 mg, 0.3 mg, 0.4 mg, 0.5 mg, 1 mg, 2 mg, 2.5 mg, 3 mg, 4 mg, 5 mg, 7.5 mg, 10 mg, 15 mg, 20 mg, 25 mg, and 30 mg per day.

The compositions can contain the cannabinoid in concentrations from about 0.01% by weight to about 80% by weight. For example, the concentration of cannabinoid can be 0.01%, 0.05%, 0.1%, 0.25%, 0.5%, 1%, 2.5%, 5%, 10%, 20%, 25%, 50%, 75%, and 80%.

Any of the cannabinoids described supra, can be formulated with appropriate excipients known in the art. The formulation can be, e.g., a liquid or semi-solid, a solution, a suspension, an emulsion, a gel, a cream, a lotion, an ointment, or a patch. Delivery can be simple or actively assisted by an electric current or other electrophysical device. For example, the cannabinoid-containing composition can be administered by applying it to the forehead. In an alternative embodiment, the composition can be administered by iontophoresis or by subcutaneous or intradermal injection to the forehead.

The cognitive or emotional impairment that can be treated by the above-described method is induced by radiotherapy, chemotherapy, or a combination of both. In an embodiment, the cognitive or emotional impairment is induced by a chemotherapy agent, e.g., a taxane, a platinum compound, a vinca alkaloid, thalidomide, bortezomib, bevacizumab, corticosteroids, or combinations thereof.

As mentioned above, provided is the use of a topical cannabinoid composition for treating radiotherapy or chemotherapy-associated cognitive or emotional impairment in a subject.

The topical composition contains a cannabinoid selected from dronabinol, cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, anandamide, virodhamine, noladin ester, 2-arachidonoylglycerol, and nabilone.

In a preferred embodiment, the topical composition for use in treating radiotherapy or chemotherapy-associated cognitive or emotional impairment contains dronabinol or Δ9-tetrahydrocannabinol. The composition, in a particular embodiment, contains dronabinol.

The topical composition is used for treating radiotherapy or chemotherapy-associated cognitive or emotional impairment by topically administering it to an area of the face of the subject not including the palpebral part of the eye. The area of the face of the subject not including the palpebral part of the eye can be the forehead above the eyebrows, the temple area between the end of the eyebrow and the hairline including the temple region, the upper cheek, or the sides or bridge of the nose.

Alternatively, the topical composition can be used for treating radiotherapy or chemotherapy-associated cognitive or emotional impairment by topically administering it to the back of the neck of a subject.

The subject can suffer from cognitive or emotional impairment induced by a taxane, a platinum compound, a vinca alkaloid, thalidomide, bortezomib, bevacizumab, corticosteroids, or combinations thereof.

The topical compositions mentioned for use in treating radiotherapy or chemotherapy-associated cognitive or emotional impairment can be formulated such that the dosage of cannabinoid is 0.01 to 30 mg per day can be administered topically to the subject.

Also disclosed is a method for treating a tumor. The method includes the steps of identifying a subject having a tumor and administering to the subject a chemotherapy agent, radiation, or both a chemotherapy agent and radiation, together with topically administering a composition containing a cannabinoid.

A subject having had surgery to remove a tumor can also be treated by administering to the subject a chemotherapy agent, radiation, or both a chemotherapy agent and radiation, together with topically administering a composition containing a cannabinoid.

Any of the cannabinoids listed above can be administered by this method. In a preferred embodiment, the cannabinoid is $\Delta^9$-tetrahydrocannabinol. In a particularly preferred embodiment, the cannabinoid is dronabinol.

Topical administration can be, e.g., applying the composition to the skin or mucous membranes. Locations for topically administering the composition are set forth above. In a preferred embodiment, the cannabinoid-containing composition is applied topically to the face to the regions that are outside of the palpebral part of the eye. In another preferred embodiment, the cannabinoid-containing composition is applied topically to the back of the neck.

The dosage of cannabinoid topically administered can be 0.01-30 mg per day. In a particular embodiment, 2-2.5 mg of dronabinol or $\Delta$9-tetrahydrocannabinol is administered topically to treat the tumor.

As mentioned above, the cannabinoid is administered topically to a subject undergoing radiotherapy and/or chemotherapy. Topically administering a cannabinoid to a patient being treated with a chemotherapy agent potentiates the action of the agent. For example, a tumor that has recurred after treatment with a particular chemotherapy agent can be successfully treated with the same agent if co-administered with a topical cannabinoid.

Any number of chemotherapy agents can be administered with a topically delivered cannabinoid. For example, chemotherapy agents such as a taxane, a platinum compound, a vinca alkaloid, thalidomide, bortezomib, bevacizumab, corticosteroids, or combinations thereof can be co-administered with a cannabinoid. In a particular embodiment, the chemotherapy agent is topotecan, bevacizumab, temozolamide, etoposide, carboplatin, irinotecan, lomustine, or mixtures thereof.

The tumors which can be treated by the above-described method can be, e.g., a brain tumor, a nervous system tumor, a head and neck tumor, or an endocrine tumor.

Brain and other nervous system tumors which can be treated with a combination of topical dronabinol and radiotherapy/chemotherapy include, but are not limited to tumors of neuroepithelial tissue, pilocytic astrocytoma, diffuse and anaplastic astrocytoma, glioblastoma, oligodendroglioma, anaplastic oligodendroglioma, mixed glioma, glioma embryonal/primitive/medulloblastoma, ependymoma, hemangioblastoma, pineal region tumors, pituitary tumors, tumors of cranial and spinal nerves, nerve sheath tumor, acoustic neuroma, meningioma, germ cell tumors and cysts, tumors of sellar region, and lymphomas and hematopoietic neoplasms of the brain.

In one embodiment, the tumor is a glioblastoma. In a particular embodiment, the glioblastoma is a tumor recurring after extirpation and treatment of a primary tumor.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

EXAMPLES

Example 1

Amelioration of Chemo Brain and Brain Fog Induced by Long Term Chemotherapy and Radiation Treatment by Daily Low-Dose Topical Administration of Dronabinol A 44 year old male was diagnosed with glioblastoma in February 2010 and underwent immediate surgery to remove the tumor. Within 6 weeks of the surgery, he began radiotherapy and chemotherapy with a combination of temozolamide, topotecan, and bevacizumab. The chemotherapy proceeded until December 2012, at which time it was discontinued, as the patient developed hypertension and proteinuria induced by the chemotherapy agents.

During the chemotherapy treatment period from 2011 through the end of 2012, the patient, a practicing attorney, regressed mentally such that he needed full time assisted caretaking. He demonstrated emotional and social withdrawal, cognitive impairment, e.g., knew what word he wanted to use but could not get it out, a decline in recognition and less connection between recognition and emotion. These mental deficits did not occur suddenly, as the patient had returned to his law practice post-surgery in 2010. The cognitive decline was not due to recurrence of the tumor, as such a recurrence was not observed during this time period. The evaluating physicians concluded that he had reached a plateau as to his mental state.

Beginning in December of 2012 and continuing through March of 2014, the patient, who was not undergoing any chemotherapy at this time, was treated daily with 2.5 mg of dronabinol applied to his forehead. Daily evaluation by his caretaker and quarterly evaluations by a medical institution were documented during this treatment period. Importantly, no hallucinatory or adverse cognitive effects were observed during the dronabinol treatment period.

Within 1-2 days after the initiation of dronabinol treatment, the patient demonstrated signs of improved recognition, memory, and social interaction. A broad range of cognitive functions, emotional skills, and social interaction skills showed daily and long term improvement. His recall and memory improved, as well as his vocabulary, attention span, interactivity, motivation, sense of humor and emotional connections generally showed improvement, including a reduction in expression of fear and caution, e.g., fear of falling.

In September 2013, his doctors were surprised by his improvement and optimistic regarding his condition. The doctors reversed their prior conclusion that his mental state had plateaued and suggested physical and speech therapy.

Example 2

Treatment of Chemo Brain and Brain Fog Induced by Short-Term Chemotherapy with Low Dose Topical Dronabinol In March of 2014, the patient described in Example 1 suffered a recurrence of the glioblastoma. More specifically, a golf ball-sized recurrence of the primary tumor which had been extirpated in 2010 was observed. At the time the tumor recurrence was detected, the patient's cognitive, social, and emotional abilities were in an improved and highly functional state as compared to that prior to dronabinol treatment.

The patient was treated again with temozolamide, and bevacizumab. Within the first two weeks of chemotherapy, he suffered from brain fog quite noticeably, but in a specific pattern. To be more precise, the patient, upon awakening each morning, had regressed in cognition and emotional function.

Each morning, the patient was treated with dronabinol as described in Example 1 supra. Within 45 minutes of each dose, a significant diminishment of brain fog occurred as demonstrated by a return of mental function. The effects of dronabinol administration lasted until the following morning, with daily improvement observed over a six-week period.

Again, as mentioned above in Example 1, no hallucinatory or adverse cognitive effects were observed resulting from administration of dronabinol.

Example 3

Rapid Reversal of Progression of Recurrent Glioblastoma Upon Co-Administration of Chemotherapy Drugs and Topical Dronabinol By way of reminder, the patient described in the two examples set forth above was diagnosed with glioblastoma in February 2010. Approximately 95% of the tumor was surgically removed within 3 days of diagnosis. Following the surgery, the patient was treated with radiation, as well as by chemotherapy with a combination of temozolamide, topotecan, and bevacizumab. In November 2010 and April 2011, a PET scan was negative for any tumor progression. In May of 2011, the combination therapy was discontinued and the patient received only maintenance bevacizumab. MRI scans were performed every two months to monitor any changes in the brain.

In July 2011, an MRI showed growth of a secondary tumor. The patient resumed chemotherapy with a combination of temozolamide, etoposide, and bevacizumab. Two months later, the tumor was still enlarging. The chemotherapy regimen was changed to carboplatin, irinotecan, together with bevacizumab. An MRI in January of 2012 demonstrated continued growth of the tumor. The chemotherapy regimen was again changed to a combination of lomustine and bevacizumab, resulting in a halt in growth of the tumor. Bevacizumab use was discontinued in March 2012 due to hypertension and proteinuria, and lomustine was discontinued in December 2012 for the same reason.

As mentioned above, the patient was treated with 2.5 mg topical dronabinol beginning in December 2012 and continuing to the present.

An MRI performed on Dec. 6, 2013 showed an increase in size of the primary tumor. On Mar. 19, 2014, a further increase in size of the tumor was noted. The secondary tumor was unchanged.

In early April 2014, the patient was again treated with temozolamide and bevacizumab. Notably, the topical dronabinol administration was continued during this round of chemotherapy. On May 21, 2014, only 6 weeks after initiation of the chemotherapy, an MRI revealed shrinkage of both the primary tumor that had regrown into the extirpated space and the secondary tumor.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

The invention claimed is:

1. A method for treating a tumor in a subject, wherein the subject has been diagnosed with a tumor or the subject has had surgery to remove a tumor, the method comprising administering to the subject a chemotherapy agent and/or radiation, and topically administering a composition containing a cannabinoid, wherein the cannabinoid is selected from the group consisting of dronabinol, cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, anandamide, virodhamine, noladin ester, 2-arachidonoylglycerol, and nabilone; the composition is topically administered to the back of the neck of the subject or to an area of the face of the subject not including the palpebral part of the eye; a dosage of cannabinoid administered topically to the subject is 0.01-30 mg per day; and the tumor is a brain tumor, a nervous system tumor, a head and neck tumor, or an endocrine tumor.

2. The method of claim 1, wherein the cannabinoid is dronabinol or Δ9-tetrahydrocannabinol and the dosage of cannabinoid is 0.1-10 mg per day.

3. A method for treating a tumor in a subject, wherein the subject has been diagnosed with a tumor or the subject has had surgery to remove a tumor, the method comprising administering to the subject a chemotherapy agent and/or radiation, and topically administering a composition containing a cannabinoid, wherein the cannabinoid is dronabinol or Δ9-tetrahydrocannabinol; the composition is topically administered to the back of the neck of the subject or to an area of the face of the subject not including the palpebral part of the eye; the tumor is a brain tumor, a nervous system tumor, a head and neck tumor, or an endocrine tumor; and a dosage of dronabinol or Δ9-tetrahydrocannabinol administered topically to the subject is 0.01-30 mg per day.

4. A method for treating a tumor in a subject, wherein the subject has been diagnosed with a tumor or the subject has had surgery to remove a tumor, the method comprising administering to the subject a chemotherapy agent and/or radiation, and topically administering a composition containing a cannabinoid, wherein the tumor is a glioblastoma and a dosage of cannabinoid administered topically to the subject is 0.01-30 mg per day.

5. The method of claim 4, wherein the composition is topically administered to the back of the neck of the subject or to an area of the face of the subject not including the palpebral part of the eye.

6. A method for treating a tumor in a subject, wherein the subject has been diagnosed with a tumor or the subject has had surgery to remove a tumor, the method comprising administering to the subject a chemotherapy agent and/or radiation, and topically administering a composition containing a cannabinoid, wherein the tumor is a glioblastoma proliferating from a primary tumor after complete or partial extirpation and treatment of the primary tumor or of a secondary tumor.

7. The method of claim 6, wherein the composition is topically administered to the back of the neck of the subject or to an area of the face of the subject not including the palpebral part of the eye.

8. The method of claim 7, wherein the cannabinoid is dronabinol and the dronabinol is administered subsequent to or together with administering a taxane, a platinum compound, a vinca alkaloid, thalidomide, bortezomib, a corticosteroid, topotecan, bevacizumab, temozolamide, etoposide, carboplatin, irinotecan, lomustine, or a combination thereof.

* * * * *